(12) United States Patent
Toumazou et al.

(10) Patent No.: US 10,922,397 B2
(45) Date of Patent: Feb. 16, 2021

(54) METHOD AND DEVICE FOR COMPARING PERSONAL BIOLOGICAL DATA OF TWO USERS

(71) Applicant: DNANudge Limited, London (GB)

(72) Inventors: Christofer Toumazou, London (GB); Georgina Toumazou, London (GB)

(73) Assignee: DNANUDGE LIMITED, London (GB)

( * ) Notice: Subject to any disclaimer, the term of this patent is extended or adjusted under 35 U.S.C. 154(b) by 0 days.

(21) Appl. No.: 16/733,630

(22) Filed: Jan. 3, 2020

(65) Prior Publication Data

US 2020/0143027 A1    May 7, 2020

Related U.S. Application Data

(63) Continuation-in-part of application No. 16/043,709, filed on Jul. 24, 2018, now Pat. No. 10,582,897, and
(Continued)

(51) Int. Cl.
| | | |
|---|---|---|
| *G06F 9/54* | (2006.01) | |
| *G06F 21/32* | (2013.01) | |
| *G06F 1/16* | (2006.01) | |
| *H04L 29/06* | (2006.01) | |
| *H04W 12/00* | (2021.01) | |

(Continued)

(52) U.S. Cl.
CPC ............. *G06F 21/32* (2013.01); *G06F 1/163* (2013.01); *G06F 16/24* (2019.01); *G06F 16/953* (2019.01); *G06F 21/35* (2013.01); *G06Q 30/0631* (2013.01); *G16B 20/20* (2019.02); *H04L 63/0442* (2013.01); *H04W 4/21* (2018.02);
(Continued)

(58) Field of Classification Search
CPC .... G06F 9/546; G06Q 10/10; H04L 29/08072
USPC .................................. 719/313; 709/204, 217
See application file for complete search history.

(56) References Cited

U.S. PATENT DOCUMENTS

| | | |
|---|---|---|
| 6,711,414 B1 | 3/2004 | Lightman et al. |
| 9,013,300 B2 | 4/2015 | Felix |

(Continued)

FOREIGN PATENT DOCUMENTS

| | | |
|---|---|---|
| EP | 2416269 A2 | 2/2012 |
| JP | 2002056278 A | 2/2002 |

(Continued)

*Primary Examiner* — Andy Ho
(74) *Attorney, Agent, or Firm* — Saul Ewing Arnstein & Lehr LLP

(57) ABSTRACT

A computer-implemented method of comparing one or more genetic traits of two users. Each user has a wearable device storing data indicative of the one or more genetic traits, the data having been obtained by an analysis of a biological sample provided by the user. The method comprises: transmitting the data indicative of the one or more genetic traits from a first of the wearable devices to a first computer device using a short-range wireless data connection; transmitting the data from the first computer device to a second computer device over a data network; transmitting the data from the second computer device to a second of the wearable devices over a short-range wireless data connection; and comparing the data from the first wearable device with the data stored on the second wearable device to determine whether there is a match between the users' one or more genetic traits.

19 Claims, 4 Drawing Sheets

Related U.S. Application Data a continuation-in-part of application No. PCT/GB2019/052069, filed on Jul. 24, 2019.

(51) Int. Cl.
    *G06F 21/35*      (2013.01)
    *G16B 20/20*      (2019.01)
    *G06F 16/953*      (2019.01)
    *G06F 16/24*      (2019.01)
    *H04W 4/80*      (2018.01)
    *H04W 4/21*      (2018.01)
    *G06Q 30/06*      (2012.01)

(52) U.S. Cl.
    CPC ......... *H04W 4/80* (2018.02); *H04W 12/0013* (2019.01)

(56) References Cited

U.S. PATENT DOCUMENTS

| | | | |
|---|---|---|---|
| 9,724,023 B2 * | 8/2017 | Swenson | A61B 5/14539 |
| 9,775,015 B1 | 9/2017 | Mishra et al. | |
| 9,858,799 B1 | 1/2018 | Deluca et al. | |
| 9,901,301 B2 | 2/2018 | Brenner et al. | |
| 2003/0208110 A1 | 11/2003 | Mault et al. | |
| 2003/0226695 A1 | 12/2003 | Mault | |
| 2005/0021679 A1 | 1/2005 | Lightman et al. | |
| 2006/0256074 A1 | 11/2006 | Krum et al. | |
| 2008/0208971 A1 | 8/2008 | Costin et al. | |
| 2013/0268292 A1 | 10/2013 | Kim et al. | |
| 2015/0073907 A1 | 3/2015 | Purves et al. | |
| 2015/0112857 A1 | 4/2015 | Gellis et al. | |
| 2016/0071423 A1 | 3/2016 | Sales et al. | |
| 2016/0219124 A1 | 7/2016 | Elgrichi | |
| 2017/0098268 A1 | 4/2017 | Karvela et al. | |
| 2017/0323057 A1 | 11/2017 | Karvela et al. | |
| 2018/0053242 A1 | 2/2018 | Agrawal | |
| 2018/0140203 A1 | 5/2018 | Wang et al. | |
| 2018/0144101 A1 * | 5/2018 | Bitran | G16H 40/20 |
| 2018/0236242 A1 | 8/2018 | Balinski et al. | |
| 2018/0263539 A1 * | 9/2018 | Javey | A61B 5/6833 |

FOREIGN PATENT DOCUMENTS

| | | |
|---|---|---|
| JP | 2002366888 A | 12/2002 |
| JP | 2005157985 A | 6/2005 |
| JP | 2013191048 A | 9/2013 |
| JP | 2014525094 A | 9/2014 |
| WO | 0113317 A2 | 2/2001 |
| WO | 02063415 A2 | 8/2002 |
| WO | 03/105445 | 12/2003 |
| WO | 2012/135557 | 10/2012 |
| WO | 2013010685 A1 | 1/2013 |
| WO | 2015050174 A1 | 4/2015 |
| WO | 2015/077512 | 5/2015 |

* cited by examiner

ND DEVICE FOR COMPARING
METHOD AND DEVICE FOR COMPARING PERSONAL BIOLOGICAL DATA OF TWO USERS

CROSS-REFERENCE TO RELATED APPLICATIONS

This application is a continuation-in-part of U.S. application Ser. No. 16/043,709, filed on Jul. 24, 2018, and is also a continuation-in-part of International Application No. PCT/GB2019/052069, filed on Jul. 24, 2019, the entire contents of each being fully incorporated herein by reference.

TECHNICAL FIELD OF THE INVENTION

The present invention relates to a method and wearable device for comparing personal biological data of two users.

BACKGROUND OF THE INVENTION

Semiconductor, nanotechnology and optical technologies have made significant contributions to people's lifestyle, especially by facilitating hardware miniaturisation. Its application to the sequencing and genotyping industry has enabled so-called "lab-on-chip" systems. Depending on the biological questions/genes of interest, primer(s)/probe(s)—more generally referred to as "biomarkers"—are designed accordingly. A biomarker is an oligonucleotide such as a DNA molecule and may target certain gene(s)/variation(s). A biomarker may alternatively, for example, be an antibody or an antigen. By applying/choosing different types of biomarkers on such systems, a customer can test his/her biological sample, DNA, RNA, protein etc, (extracted locally or remotely by a third party from e.g. saliva, blood, urine, tissue, stool, hair etc) for specific traits, possibly as dictated by certain lifestyle concerns or interest.

Such "personal" genetic or biological information enables medical decisions to be made more effectively, for example, by selecting treatments or drug doses which are more likely to work for particular patients. Identifying individual differences at a molecular level also allows lifestyle and dietary advice to be tailored according to the needs of individuals or particular classes of individuals. For example, personal care products such as cosmetics, cosmeceuticals and nutraceuticals may be selected based on how effective these products are for individuals having certain single nucleotide polymorphisms (SNPs) in their DNA. A number of private companies have been created in order to cater for the growing consumer genetics market and every day new genetic traits are being described, generating a continuously expanding catalogue of biomarkers that have the potential to offer insight into the health, wellbeing, and, in the case of genetic variations, phenotype, of a great many people.

Whilst such "unlocking" of an individual's genetic data as described above may benefit the individual in many different ways, the abstract nature of the data may make it difficult for the individual to appreciate its value. For example, individuals may not feel that they have "ownership" of their data or they may feel they are unable themselves to make use of their data because of its complexity or inaccessibility. Privacy concerns may also dissuade individuals from making use of their data.

U.S. Ser. No. 10/043,590B2 describes a wearable device for providing product recommendations based on a user's biological information, such as genetic data. The wearable device incorporates a laser scanner or barcode reader which the wearer of the device uses to identify a product he or she is interested in purchasing or consuming. The device then provides an indication whether or not the product is recommended for the wearer based on his or her biological information. For example, an analysis of a user's DNA may have revealed that the user metabolises caffeine more slowly than most other people, in which case, the wearable device may recommend that he or she avoids coffee. Users of the wearable device described in U.S. Ser. No. 10/043,590B2 are, however, not easily able to compare product recommendations or biological information with one another. Whilst two users may, for example, scan the same product and see whether or not the indication provided by their respective wearable devices is the same, this process can be laborious and does not necessarily allow users to identify which aspects of their biological or genetic identities are different or which aspects they may have in common. Users can of course discuss their biological information while simultaneously viewing the information on their smartphones. Nonetheless, a fast, almost instantaneous, method of comparing information is desirable.

SUMMARY OF THE INVENTION

According to a first aspect of the present invention there is provided a computer-implemented method of comparing one or more genetic traits of two users. Each user has a wearable device storing data indicative of the one or more genetic traits, the data having been obtained by an analysis of a biological sample provided by the user. The method comprises: transmitting the data indicative of the one or more genetic traits from a first of the wearable devices to a first computer device using a short-range wireless data connection; transmitting the data from the first computer device to a second computer device over a data network; transmitting the data from the second computer device to a second of the wearable devices over a short-range wireless data connection; and comparing the data from the first wearable device with the data stored on the second wearable device to determine whether there is a match between the users' one or more genetic traits.

The method may further comprise operating an indicator at the second wearable device and/or the second computer device to provide a visual, audio or other sensory indication of the result.

The data indicative of the one or more genetic traits may comprise data indicative of nutrition- and/or skin-related genetic traits.

Each short-range wireless data connection may conform to a Bluetooth protocol, preferably a Bluetooth Low Energy profile, or a near-field communication protocol.

Each short-range wireless data connection may be established by detecting that the respective wearable device is within a predefined distance of, or in contact with, the respective computer device, preferably wherein said predefined distance is less than 10 cm, or more preferably, less than 5 cm.

Each wearable device may be a wrist-worn device and/or each computer device is a portable computer device, preferably a smartphone.

The method may comprise, at the first computer device, receiving an invitation to compare one or more genetic traits with another user. The invitation may comprise data indicative of the one or more genetic traits of the other user. The invitation may be sent in response to one of the users identifying the other user using an online search tool. The data transmitted from the first wearable device may be encrypted using a public encryption key associated with or included in the invitation. The second wearable device may store a corresponding private key for decrypting data encrypted using the public key.

The method may comprise switching the first user device to a mode for establishing a short-range wireless data connection with the first wearable device in response to receiving user input indicative of the invitation being accepted. The method may also comprise forming a connection between the respective users in a social network in response to receiving user input indicative of the invitation being accepted. The user may accept the invitation using the wearable device, preferably by pressing a button on the wearable device or performing a gesture using the wearable device.

The data may only be made available to the second wearable device if the one or more servers of the data network have received data indicative of one or more genetic traits stored on the second wearable device.

The method may comprise, at either of the computer devices or wearable devices, receiving a user selection of which one or more genetic traits are to be compared.

The data from the first wearable device may be deleted from the second wearable device after a predetermined time.

Each wearable device may store user activity data indicative of one or more physiological and/or biochemical functions of the user, or indicative of a user environment. The method may further comprise, in response to determining that there is a match between the users' one or more genetic traits, comparing the user activity data of the first wearable device with the user activity data of second wearable device to determine whether there is a match between the users' behaviours as indicated by the respective data.

Each wearable device may be configured to provide product recommendations in respect of one or more consumable, topically applied and/or body-worn products, the product recommendations being modulated for each user depending on the user activity data, and wherein the compared user activity data comprises data indicative of one or more product recommendations having been modulated.

According to a second aspect of the present invention, there is provided a computer-implemented method for authenticating a user of a computer system. The method comprises, at the computer system: establishing a short-range wireless data connection to a wearable device storing user data obtained by an analysis of a biological sample provided by the user; receiving authentication data from the wearable device over the short-range wireless data connection, the authentication data being derived using the user data; and authenticating the user by verifying that the received authentication data is derived from the user data.

Verifying that the received authentication data is derived from the user data may comprise determining whether the received authentication data matches corresponding authentication data stored by the computer system.

The user data may comprise data indicative of one or more genetic traits, preferably data indicative of nutrition- and/or skin-related genetic traits.

The wearable device may be a wrist-worn device and/or the computer device may be a portable computer device, such as a smartphone.

According to another aspect of the present invention there is provided a wearable device comprising a memory storing data associated with a personal biology of a user, a short-range wireless transceiver for receiving, from a peer wearable device, data associated with a personal biology of a peer user, and a processor for comparing the received data with the data stored in the memory in order to determine whether or not there is a match. The device further comprises an indicator for generating a visual, audio or other sensory indication of a match when the data is determined to match.

The device may be operable to receive the data from a peer wearable device in response to detecting that the peer wearable device is within a predefined distance or is in contact. The step of detecting that the other wearable device is within a predefined distance of the wearable device may comprise detecting that the strength or quality of a signal transmitted from the peer wearable device exceeds a predefined value. The transceiver may operate using Bluetooth protocol, preferably a Bluetooth Low Energy profile, or a near-field communication protocol. The predefined distance may less than 10 cm, preferably less than 5 cm, or possibly less than 0.5 cm.

The indicator may be configured to generate a visual, audio or other sensory indication of a non-match when the data does not match.

The data associated with a personal biology of a user may comprise one or more scores, the or each score indicating whether the user is predisposed to or has an associated personal behaviour or condition. By way of example, the data may indicate a user's ability to metabolise caffeine, his or her sensitivity to calories and carbohydrates etc, all of which characteristics are derivable from an analysis of certain parts of the user's genetics.

The wearable device is a wrist-worn device, e.g. comprising a wristband or wrist strap.

The transceiver may be configured to transmit the data associated with a personal biology of a user stored in said memory, to the peer device, in response to detecting that the peer device is within a predefined distance or in contact.

The wearable device may comprise a sensor, such as an accelerometer, for detecting a user input or gesture. The device is configured upon detection of such an input or gesture to switch from a first mode in which data is not exchanged with a peer device to a second mode in which data is exchanged.

The device may comprise a memory storing product codes and product code recommendations, and a product code reader for reading a product code from a product. The processor may configured to obtain a product recommendation for a read product code and said indicator is configured to generate a visual, audio or other sensory indication of the obtained product recommendation. The product code reader may be a barcode scanner.

The wearable device may be a smartphone.

According to a yet further aspect of the present invention there is provided a system for allowing a user to compare data, associated with his or her personal biology, with a peer user. The system comprises a wearable device according to the above first aspect of the invention and a computer device in wireless communication with said wearable device, the computer device allowing the user to select the data on which the match is to be carried out from a set of data stored in the memory of the wearable device. The wearable device may be a wrist-worn device and the computer device may be a smartphone.

According to another aspect of the present invention there is provided a computer-implemented method of comparing data associated with personal biologies of respective users stored on respective wearable devices. The method comprises detecting by the wearable devices that the wearable devices are within a predefined distance of each other or in contact with each other and, in response to said detection, exchanging said data between the devices via a wireless interface. The method further comprises comparing the data of the users at one or both of the devices to determine whether or not the data matches, and operating an indicator at one or both of the devices to provide a visual, audio or other sensory indication of a match when the data is determined to match.

The method may comprise providing individual selection or deselection control of categories of biological information to be shared with others through external computer devices such as smartphones in communication with said wearable devices.

According to a further aspect of the present invention there is provided a method of allowing users to remotely compare their genetic traits. The method comprises: storing first information relating to a first user's genetic traits in a computer memory of a wrist worn device computer device; transmitting said first information from the wrist worn computer device to a further computer device via a short range wireless data connection; further transmitting said first information to a network server and/or to a second user's computer device; at said network server or said second user's computer device, comparing said first information against second information relating to said second user's genetic traits to determine an extent to which they match; and transmitting from said network server or said second user's computer device data indicating said extent.

DETAILED DESCRIPTION OF THE INVENTION

Figure 1:
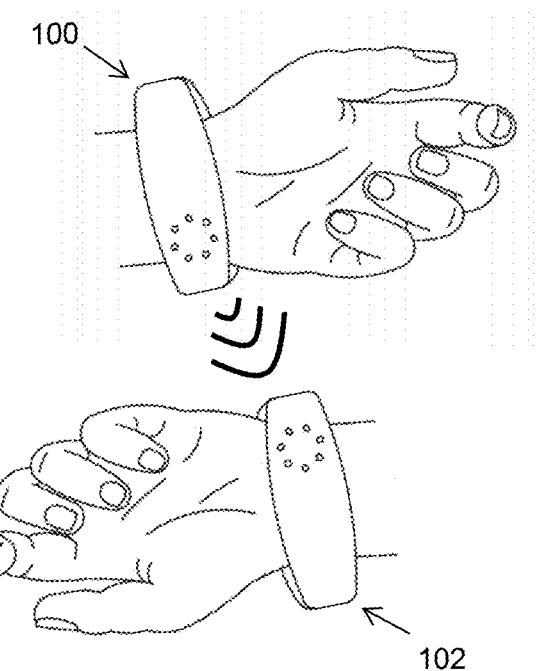
FIG. 1 illustrates schematically a pair of users exchanging personal biological information using wearable devices.

The embodiments described here aim to address the problems described above by allowing users to compare their personal biological information in a way which is convenient and secure. This personal biological data is typically data derived from a person's biology, e.g. genetic traits. The personal biological information is stored on a wearable device which comprises a transmitter and receiver for transferring the biological data from between wearable devices when they are brought close to or in contact with one another. After the biological data has been exchanged, the wearable device compares the two sets of data to determine aspects of the data which are common to both users and/or the differences between the two sets of data. Performing the comparison at the wearable device helps ensure that the process is quick and reliable, e.g. because communication with a remote server is not required. This does not preclude of course the involvement of a remote server (e.g. in the "cloud"). The results of the comparison are then presented to the users. For example, although a pair of friends/users may each know that they themselves have gluten intolerance, they may otherwise be unaware that their friend has the same intolerance. Conversely, one user may have a predisposition which requires them to abstain from eating too much red meat, whereas another user may be predisposed to anaemia, requiring them to eat an iron/meat rich diet. Comparisons based on the biological information of the two users may therefore encourage them discuss how to best manage a particular condition or to decide on a meal they can share or a restaurant which is appropriate for them both.

Allowing users to "share and compare" their biological information with a simple cooperative gesture provides a playful and social dimension to what might otherwise seem to the users to be a fairly abstract exercise. For example, when there is a "match" for the biological information of two users then the social connection between those users may be reinforced, or the process of making the comparison may act as an "icebreaker" for further interactions and discussions between the two users. Furthermore, these social aspects may encourage the users to have a greater awareness of their biological identities and lead or "nudge" them towards making better health and lifestyle decisions.

The personal biological data that is compared is not limited to data relating to nutrition but can extend to any characteristics that are derived from personal biological data. For example, data that is compared may relate to skincare and cosmetics/cosmeceuticals, fitness/activity, smoking, alcohol, etc.

The personal biological information of a user may comprise personal genetic or epigenetic data or proteomic data, obtained by an analysis of a biological sample (e.g. a mouth swab) provided by the user. For example, the biological sample can be analysed using primers, strands of short nucleic acid sequences that serve as a starting point for DNA synthesis. As is known in the prior art, such primers can be used in the detection of genetic single-nucleotide polymorphisms (SNPs) and more particularly to determine the variation type (or allele) of a tested individual for a given SNP. Alternatively, or additionally, the personal biological information may comprise information related to the microbiome of the user, such as the presence or absence of certain gut bacteria (e.g. *Helicobacter pylori*). Such microbiome data may be obtained by breath testing. The personal biological information may also comprise information about a physiological property of the user (such as the current or historic heart rate of the user), which in some cases, may be obtained by a sensing device incorporated in the wearable device.

The personal biological information may also be derived from one or more of the above types of data. For example, the personal biological data may comprise recommendations for certain products or services, or classes of product or services, which an analysis of the above types of data has revealed are particularly suitable for the user or that should be avoided by the user. These recommendations may be derived from biological filter codes which map to respective products or services or categories of products or services but do not explicitly identify a user's genetic or biological information. For example, there may be a biological filter code which indicates that a user is likely to be more adversely affected (because of his or her genetic traits) by foods with high cholesterol. In this case, by comparing the biological filter codes (or the biological information used to derive the filter codes), users are able to be see whether they are likely to be recommended similar products or services. This may encourage greater interaction and discussion between the users and may give rise to a positive "synergy" in which the users are more likely to take notice of the product recommendations and/or more likely to compare their biological data.

FIG. 1 illustrates two users exchanging personal biological information using wrist-worn wearable devices 100, 102.

In the example shown in the figure, the expanding curved lines indicate that information is being transmitted from one device 100 and received by the other device 102. In this case, a Bluetooth Low Energy (BLE) protocol is used to exchange the biological information, although other protocols designed for data transmission over relatively short distances, such as a near-field communication (NFC) protocol may be used. When an NFC protocol is used, the devices are typically required to be brought within about 5 cm of each other in order to establish a communication channel between them. ISP 1507 (NFC & ANT BLE) module based on Nordic Semiconductor nRF52 chip is used and it is integrated with Cortex M4 CPU, flash, RAM memory and optimised antenna. The range at which a "connection" is established may be (user) configurable.

Transmitting the personal biological information over only a short range means that the users are required to bring their devices into relatively close proximity. This re-assures the users that their data will not be intercepted by third-parties (introducing a high degree of privacy) and adds a social element to the process of exchanging the biological information which is similar to shaking hands, for example. In some examples, the wearable devices may be required to come into contact (or be "tapped" one against the other) in order for the exchange of data to take place or to initiate the exchange. The biological information may also be exchanged in encrypted form. For example, biological information may be encrypted using a public key associated with the intended recipient and then decrypted using the corresponding private key stored on the recipient's wearable device. The recipient's wearable device may also store the received biological information for only a short time (e.g. less than 30 s) or no longer than is necessary for performing the comparison.

Figure 2:
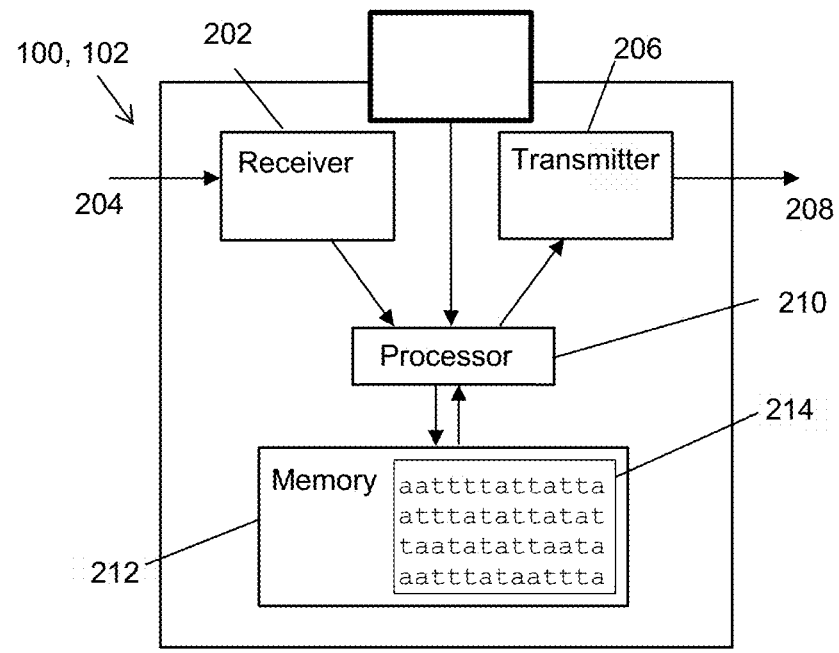
FIG. 2 is a schematic system view of the wearable device of FIG. 1.

FIG. 2 is a schematic system view of the wearable devices 100, 102 of FIG. 1. Each wearable device 100, 102 comprises a gesture sensor for triggering the mode for exchanging data, a receiver 202 for receiving data 204, and a transmitter 206 for transmitting data 208, according to a wireless communication protocol as discussed above. The gesture sensor, the receiver 202 and the transmitter 206 communicate with a processor 210 which is connected to a memory 212 which contains the personal biological information 214 of the user associated with the wearable device 100, 102. In use, the processor 210 retrieves the personal biological information 214 from the memory 212 and transmits it using the transmitter 206. Personal biological information 214 received by receiver 202 can also be stored in memory 212, allowing the processor 210 to compare the received information 214 with the information 214 of the user.

Figure 3:
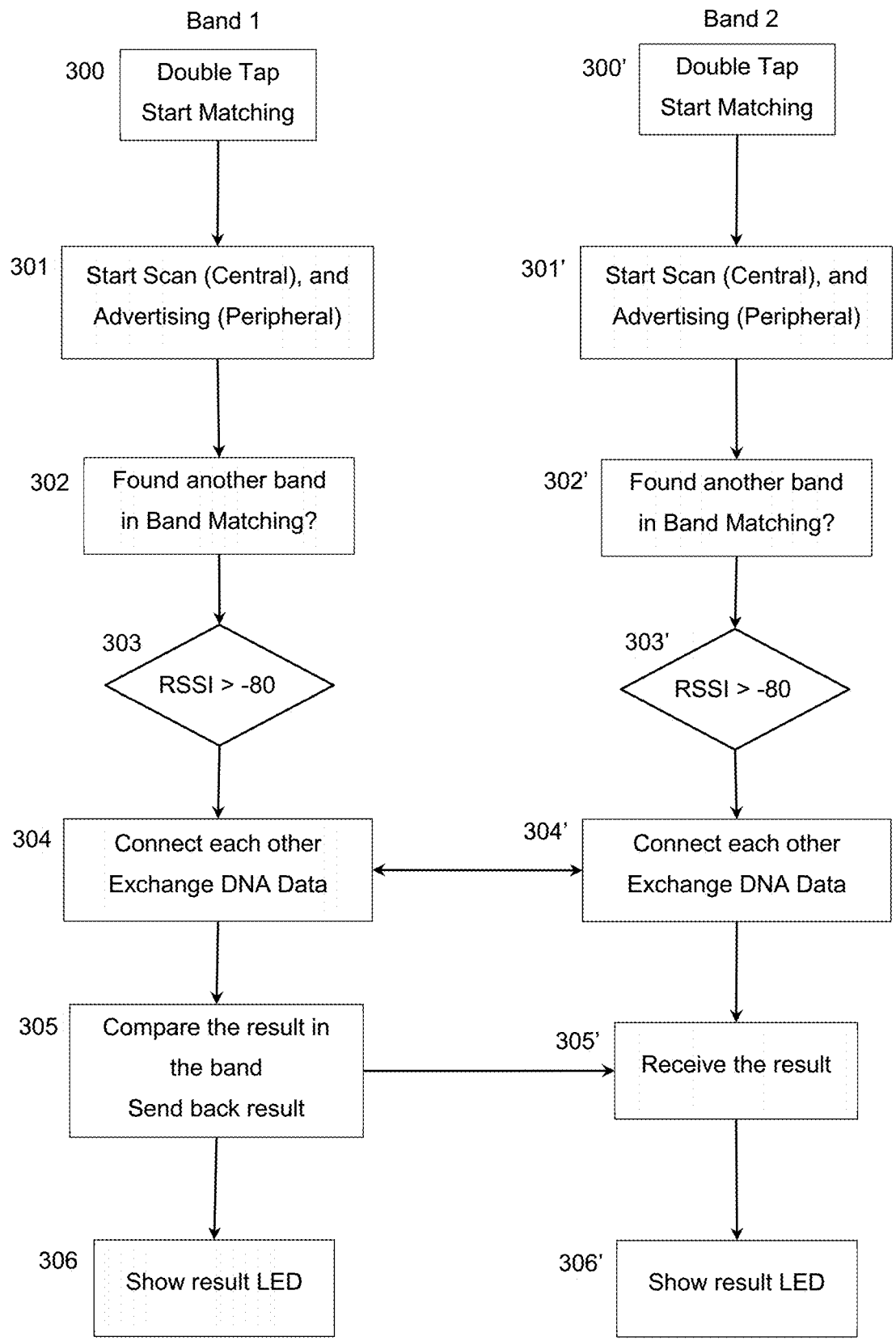
FIG. 3 is a sequence diagram further illustrating how the wearable devices of FIG. 1 can be used to exchange personal biological information.

FIG. 3 is a sequence diagram illustrating how the wearable devices 100, 102 (which are designated in the figure as "Band 1" and "Band 2") can be used to exchange personal biological information. In steps 300 and 300' the respective wearers of the bands perform an action to put the device into a "matching mode". In this example, a "double tap" gesture is used, with the gesture being detected by, for example, an accelerometer/gyroscope (MPU-6050 combining a 3-axis gyroscope and a 3-axis accelerometer) in the wearable device, though of course other gestures or modes of user input, such as a button or a touch screen, can also be used. Each device may stay in the matching mode for some pre-defined period of time, e.g. 10-15 seconds, after which the matching mode is switched off.

In steps 301 and 301' the devices scan for other devices while simultaneously advertising that they are available for matching. In steps 302 and 302', the respective devices wait until they have found another device in the matching mode. A relative received signal strength indication (RSSI) is measured by each device (steps 303 and 303'). The measured RSSI values are an indication of the power level of the signal being received by each device from the other. Typically, RSSI values may be provided according to a negative scale starting at −100 and ending at 0, with RSSI values closer to 0 indicating stronger received signals. Other scales for measuring the received signal strength can also be used, for example, decibels referenced to one milliwatt (dBm) or a received channel power indicator (RCPI) scale, which is part of the IEEE 802.11 standard. If the RSSI values exceed a certain value (e.g. RSSI>−80 or a received signal strength of −80 dBm), then the devices may connect to each other in order to exchange biological information (steps 304 and 304'). In example shown in the figure, the transfer (exchange) of biological information is unidirectional between the devices.

One of the devices (here, Band 1) receives the personal biological data from Band 2. Band 1 then compares the received biological information with the biological information stored in its memory and then transmits the result(s) of the comparison to the other device (steps 305 and 305') such that both bands now know the result. The comparison of the personal biological information of the users may be carried out in different ways depending on what type of information is exchanged. For example, if the information relates to particular genes, SNPs or DNA sequences, then the comparison may involve determining whether those genes, SNPs or DNA sequences are common to both users. Similarly, if the personal biological information comprises a set of biological filter codes for each user then these sets can be compared to see if there is any overlap. The comparison may also involve determining the probability that the users have a particular characteristic in common in order to provide the users with a measure of how likely or rare it is they share that characteristic.

The results of the comparison may be presented to each user by, for example, illuminating a light-emitting diode (LED) (steps 306 and 306'), e.g. a green colour for the LED may indicate that there is a match between the two users' biological information, whilst a red colour may indicate no match. Other means for presenting the results of the comparison to the users may also be used, such as a display, a haptic device to apply a force or vibration to the wearer of the band, or an audible alarm or voice synthesizer. In an embodiment, each band stores the result temporarily in its RAM memory whilst displaying the result. After the elapse of some short period of time, e.g. 10 seconds, the indication is turned off and the result deleted from the memories of both bands.

Figure 4:
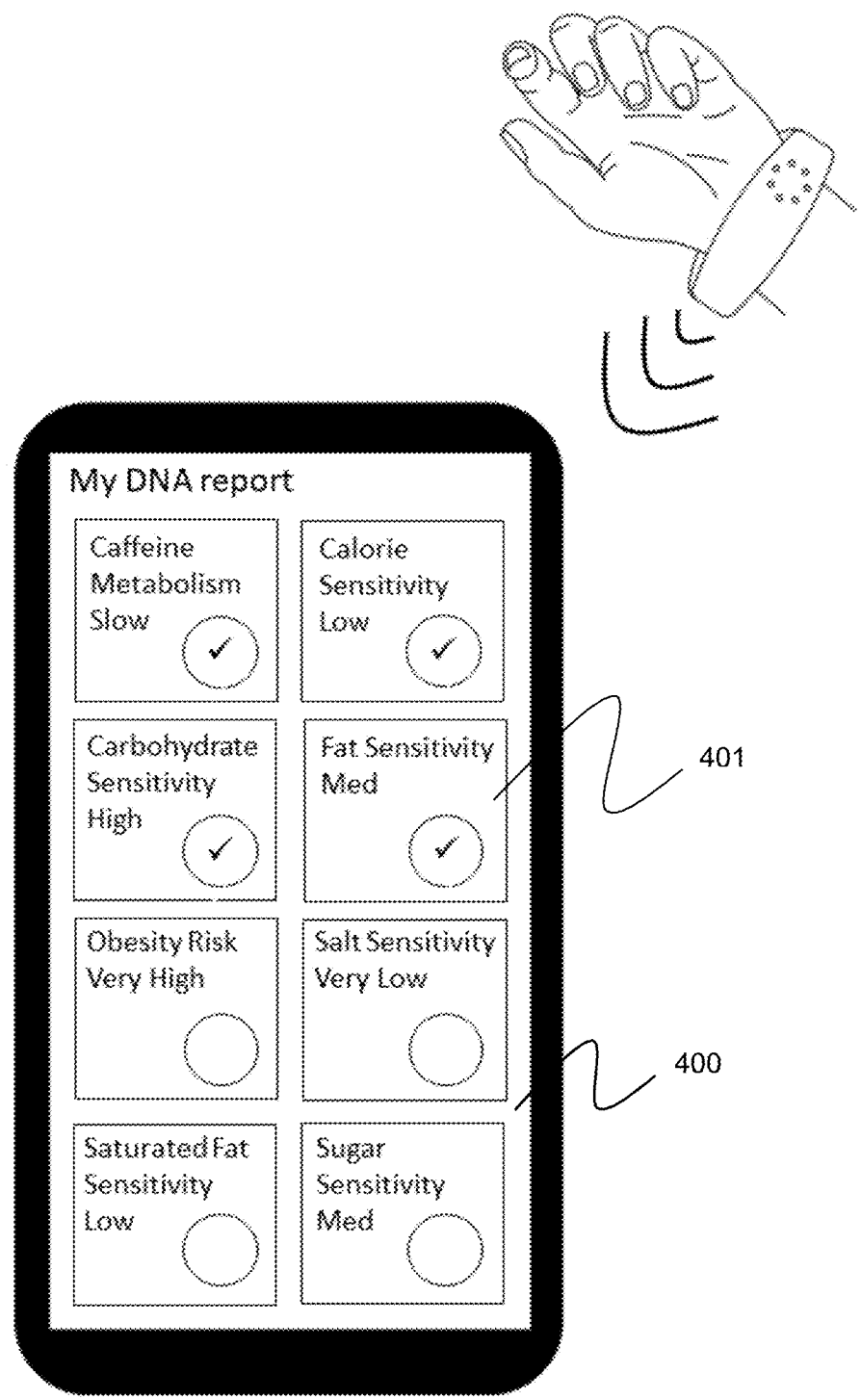
FIG. 4 is a schematic diagram illustrating a user interface for displaying a user's biological information.

The wearable device is likely to have limited means for accepting user inputs. The device may therefore be able to communicate with an external computer device such as a smartphone, e.g. using a Bluetooth interface. The smartphone may be configured with an app that allows the user to control settings on the wearable device. FIG. 4 illustrates a graphical user interface 400 that is provided on a smartphone display, via an installed app, for displaying information associated with a user's personal biological information. In this example, the personal biological information comprises numerical scores for categories such "Calorie sensitivity" or "Fat sensitivity". The numerical scores are mapped to user friendly text descriptions such as "Very High", "High", "Med", "Low" or "Slow" for presentation in the user interface. The different categories are presented as graphical user elements 401. In some implementations, the user may select or deselect the graphical user elements individually in order to control whether the biological information associated with that category should be shared with other users and/or used when comparing the users' biological information. In FIG. 4 for example, the user has selected four panels for sharing, namely "Caffeine Metabolism", "Calorie Sensitivity", "Carbohydrate Sensitivity", and "Fat Sensitivity (shown with selection in the Figure). Such control may be useful for users to avoid revealing, either directly or indirectly, information which they would rather remain private. Comparison of two users' biological information may comprise comparing the numerical scores in each of the categories to determine whether or not any of the scores either match or are approximately the same, i.e. differ by only a small relative or absolute amount. Alternatively, weighted differences of the scores can be used to define a similarity metric indicating how "alike" the users are.

In the case that two peer users have selected categories for matching that are different, this may be indicated by illuminating a third colour of LED, e.g. white, in order to indicate to the users that no matching is possible and that they should consider selecting different categories.

The wearable device may also report back the results of comparisons to the user's smartphone. If the identity of a peer user is known, this could allow results to be logged at the smartphone/app. Based on the results of a comparison, users might then be able to share via their smartphone information regarding purchased products, fitness, etc. In other words, the ability to compare biological related information can form a basis of many different social networking opportunities.

Although not described here in detail, it is possible that bands may be provided with product code readers to allow the bands to read product codes from products being considered for purchase or consumption. Such readers may be barcode scanners and may allow users to obtain product recommendations based upon product data stored in the bands.

It is of course possible that only one of two peer users may have a band, with the other only having a smartphone. In this case, there may be an option in the smartphone app to display a code such as a barcode on the phone's GUI which identifies the user's personal biological data. A peer user having a band can then scan that code using the band's product code reader and perform the comparison described above. Of course, in this case the result may only be displayed on the band, but that may be adequate as both users can see the result.

The above described embodiments and examples have focussed on exchanging personal biological information using peer wearable devices 100, 102 that are in close proximity to one another, e.g. using a short-range communication protocol, such as BLE. However, personal biological information may alternatively be exchanged in without requiring the wearable devices 100, 102 to be in the same geographic location. For example, a user may want to compare his or her product recommendations and/or biological information with a user who is located in another city or country. One way in which this can be done is via a social networking platform, in which one of the users sends a request (often referred to as a "friend" request) to the other user to establish a connection (i.e. association or "edge") within the social network (social graph). The other user can then accept or reject the request depending on whether he or she wishes to be connected to the other user within the social network. If the request is accepted, the users are granted permission to view data (e.g. personal biological information and/or product recommendations) associated with the other user and/or to interact with one another, e.g. by sending each other messages or communicating via a chat room interface.

In some cases, two users may become connected to each other in the social network in response to having exchanged personal biological information with one another using their wrist-worn wearable devices 100, 102. In this case, each wearable device may transfer a user identifier to the other wearable device, which is then stored at the wearable device. The user identifier may be a unique identifier that is specific to the wearable device and/or the user. The user identifier may be based in part on the user's personal biological information. When the user connects or "syncs" the wearable device 100, 102 to a networked computer device, such as the user's smartphone, the wearable device transmits the user identifier to the networked computer device, which in turn transmits the user identifier to a server 505 (or servers) forming part of a data network such as the internet, the server(s) being associated with the social network. The users may then be connected to one another in the social network automatically, e.g. by the server(s) updating a database to indicate that the users are connected to one another. Alternatively, in response to receiving the user identifiers, the server(s) of the social network may send a friend request to one or both of the users to allow the user(s) to decide whether to form a connection.

In conventional social networking applications, a user may accept or grant a friend request by interacting with a control element of a graphical user interface, e.g. by using a mouse or touchscreen to click a button on a web interface. Such a mechanism is generally appropriate when the users plan to share personal information that they do not believe is particularly sensitive or that has already be made public. However, users who are very active in a particular social network, or who are members of a multiple social networks, may receive a large number of friend requests and therefore become accustomed to accepting friend requests without considering what personal data may be made available to other users. This problem may occur, for example, when a user receives multiple friend requests from the same user relating to different social networks. In the case of a social network in which users can exchange personal biological data, privacy concerns are paramount and users may abandon the social network if there are no effective safeguards against their personal data being shared inappropriately.

A solution to these problems is provided by a mechanism for accepting a friend request in which the user responding to the request is required to use his or her wearable device 100, 102 to confirm acceptance of the friend request. For example, the user may receive the request on his or her smartphone (or other computer device), which is provided with an application that allows the request to be accepted only after the user's wearable device 100, 102 is connected (or synched) to the smartphone, e.g. using a short-range wireless communications protocol. In some cases, the application may prompt the user to connect the wearable device 100, 102 to the smartphone when the friend request is received and/or after the user has made a selection to accept the request.

Figure 5:
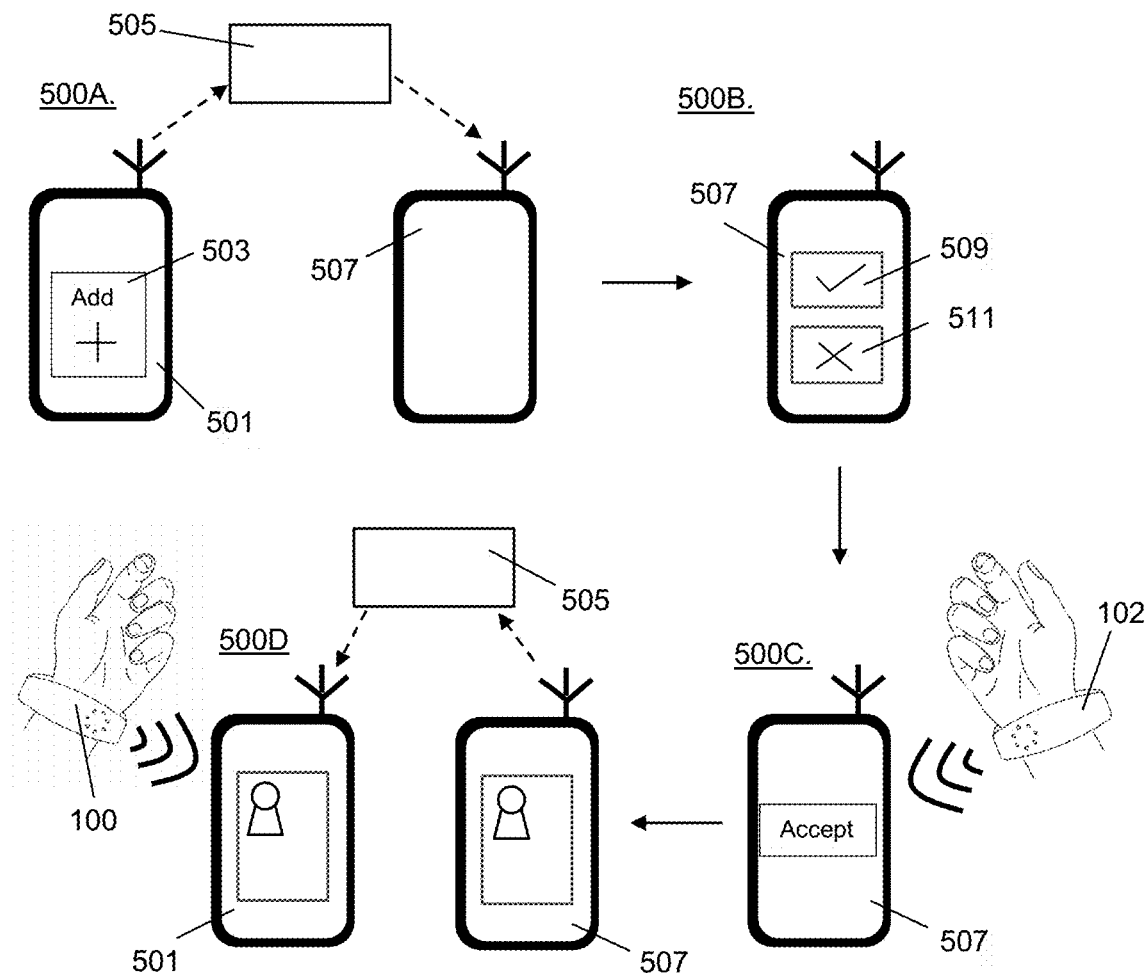
FIG. 5 is a flow diagram illustrating a method forming a connection between two users of a social network.

FIG. 5 illustrates the steps of a method for allowing two users to compare personal biological information when the users are remote from one another. In the first step 500A, a first user sends a request using his or her personal computer device (e.g. smartphone) 501 to connect with a second user. For example, the user may select or "click" a user interface control 503 on the device 501 to "Add" the other user as a friend in a social network. The personal computer device 501 transmits the request to one or more servers 505 associated with the social network using a wired or wireless data connection, e.g. a data connection to the internet or a mobile telephone data network.

In step 500B, the server(s) 505 transmits an invitation to a personal computer device 507 of the second user to invite the second user to form a social network connection with the first user. The invitation is typically presented to the second user via a user interface comprising user interface elements 509, 511 that allow the second user to indicate that he or she wants to either accept or refuse the invitation.

In step 500C, the second user's personal computer device 507 enters a mode that allows the second user to confirm acceptance of the invitation using his or her wearable device 102. For example, the second user may bring his or her wearable device 102 into proximity with the personal computer device 507 so that data indicative of the second user's acceptance can be transmitted from the wearable device 102 to the personal computer device 102 using a short-range data connection. Alternatively, the data indicative of the second user's acceptance can be transmitted to the wearable device 102 using a local area network, such as a Wi-Fi network, to which both devices are connected. The data transmitted to the wearable device 102 may comprise a user identifier for the second user and/or the user's biological data, preferably in an encrypted form, as described above.

In some cases, the second user may be required to press a button on the wearable device 102, or to perform a gesture while wearing or holding the wearable device 102 in order to put the wearable device 102 into a "matching mode" whereby data can be transmitted to and/or received from the user device 102. The wearable device 102 may also use a visual, audible or tactile indicator to indicate to the user that he or she is required to confirm acceptance of the invitation using the wearable device 102, e.g. by pressing a button on the wearable device 102 or performing a particular gesture with the wearable device 102. Alternatively, or additionally, the wearable device 1002 may require some form of biometric data specific to the user to be provided in order to accept the invitation, e.g. the camera of the wearable device may be used to record an image of the user's face, which is then processed using facial recognition software to confirm the identity of the user.

In step 500D, the second user device 597 transmits data indicative of the second user's acceptance of the friend request to the one or more servers 505 associated with the social network. The server(s) 505 transmit a request to the first user device 100 asking the user to confirm acceptance of the social network connection using his or her wearable device 100 (as described above for step 500C). In some examples, this confirmatory step may be performed by the first user as part of the first step 500A (or at some later point in time). The first user device 501 then transmits the acceptance to the server(s) 505 so that the social network connection can be formed between the two users. A user interface associated with the social network, e.g. a friend list, may be updated on each of the personal computer devices 501, 507 to show that the users are connected to one another.

In some implementations, the personal biological data (which may also be referred to as "digital DNA") is encrypted and stored locally on each of the wearable devices 100, 102. When the second user accepts the first user's friend request using his or her personal computer device 507, the second user needs to "synch" (i.e. connect) his or her wearable device 102 with the personal computer device 507 in order to transfer the second user's encrypted biological data to the personal computer device 507, e.g. using a Bluetooth connection. This process can be regarded as authenticating the user prior to the friend request being accepted. When the first user receives the friend acceptance from the second user in an application executing on the personal computer device 501, the first user needs to "synch" his or her wearable device 100 with the personal computer device 501 and transfer the first user's encrypted personal biological data to the personal computer device 501. The personal biological data of each user is transmitted between the personal computer devices 501, 507 (e.g. via a wireless mobile network or the internet), either directly between the personal computer device or via the server(s) 505. The personal biological data can then be compared (i.e. matched) at the server(s) and/or at either or both of the wearable devices 100, 102. The results of the comparison can then be indicated to the user using an indicator on the personal computer device 501, 507, such as the display screen of the device, and/or using an indicator of the wearable device 100, 102, e.g. using a colour changing LED.

As described above, the comparison of the personal biological information of the users may be carried out in different ways depending on what type of information is provided or exchanged by the users. For example, the personal biological information of each user may comprise information indicative of the user having one or more genetic traits or characteristics, e.g. whether the user has a particular gene, SNP or DNA sequence. The personal biological information may be encoded as one or more Boolean variables (e.g. one for each genetic trait), in which case a pairwise comparison between the variables is performed and the number of matching variables is then converted into a score. The personal biological information of the users is defined as matching "overall" if the score exceeds a predefined threshold, e.g. whether more than 70% of the compared variables match. Alternatively, the personal biological information may be encoded in the form of a probability or rating derived from how likely the user is to express a particular genetic trait or characteristic. In this case, the comparison is performed by determining whether the difference between the corresponding ratings for each genetic trait, or the whether the relative ratio of the corresponding ratings for each genetic trait, is less than a predefined threshold. For example, although the users may have respective scores for "Salt Sensitivity" of $^{50}/_{100}$ and $^{60}/_{100}$, the scores may nevertheless be determined to match because they differ by only 10 points. In some cases, each genetic trait is associated with a different predefined threshold. Preferably, each threshold is derived from the variance of the scores for each trait within the population of users to ensure that matches for each trait are not too rare or too frequent.

The results of comparing the users' personal biological data can be displayed using a graphical user interface on the personal computer devices 505, 507, e.g. as part of a dedicated application or "app". For example, the user interface can be similar to that shown in FIG. 4, with a collection of panels associated with each of the various genetic traits ("Caffeine Metabolism", "Carbohydrate Sensitivity" etc.). Each of the panels is modified depending on whether the two users match for the associated genetic trait, e.g. to visually de-activate or "grey out" the panel when the associated genetic trait is present in one user but not the other. The graphical user interface (or another similar interface) also provides users with the option of choosing which of their genetic traits they which to compare. In some cases, the user may be asked to select which traits he or she wishes as part of the process of creating or accepting an invitation to compare genetic traits with another user. Alternatively or additionally, the user may be able to set "global" privacy settings that prevent some or all of his or her genetic traits from being shared with other users, or conversely, allow certain traits to be always available for comparison with other users' genetic traits.

The one or more servers 505 may act as an "escrow" service in which the personal biological data of a user is only made available to another user if that other user has made his or her personal biological data available for sharing with the user. This service may be implemented by the one or more servers encrypting the biological data of a user before the data is transmitted to a wearable device 100, 102. The decryption key is then only provided to the wearable device 100, 102 once the server(s) 505 has received the other user's biological data from the wearable device 100, 102.

The above method 500A-D requires each user to perform actions that are similar to the "in-person" methods described above for comparing biological data using the peer wearable devices 100, 102, except that the short-range connection is to the user's personal computing device (e.g. smartphone), rather than directly to the other user's wearable device 100, 102. From the user's perspective, the requirement that the user must respond using the wearable device 100, 102 helps reassure the user that he or she is in control of when the biological data is shared with another user.

Considering the social network discussed above, a user who is not a member of the social network may be added as a member of a social network, or invited to join the social network, in response to his or her wearable device 100, 102 being brought into proximity with the wearable device 100, 102 of another user who is already a member of the social network. In some cases, the users may only join or only be invited to join the social network if they have matched (or possibly merely attempted to match) with a user who is already a member of the social network. In other cases, both users may be added to the social network even if neither of them is already a member. The social network may be configured to add the users as "friends" in response to a match being obtained, i.e. a link or "edge" is created in the network to join the users. The social network may also be configured to allow a user to compare their data with users who are friends of their friends without requiring "in-person" matching using their wearable devices 100, 102, i.e. a user may match with other users who are twice removed from them in the social network. This matching may involve the user inviting the other user to match and the other user accepting the invitation using the process described above.

The wearable devices 100, 102 may use end-to-end encryption to ensure that the biological information is not accessible to third parties. For example, an end-to-end encryption scheme based on public and private keys can be used in which each of the wearable devices 100, 102 is associated with a unique public encryption key that can be transmitted to the other user, e.g. by inclusion in the invitation to compare biological data or in a friend request. The public key is used by the wearable device 102 (or possibly by the personal computer device 507) to encrypt the biological information prior to transmission to the servers 505. When the encrypted biological information is received at the other wearable device 100, it is decrypted using a private key that corresponds to the public key. Preferably, the private key is stored securely on the wearable device 100 so that no other device is able to decrypt information that has been encrypted using the corresponding public key. The wearable device may store the received encrypted data (and/or the decrypted data) for only a short time (e.g. less than 30 s) or no longer than is necessary for performing the comparison. In some systems, the system may be configured to ensure that no copy of a user's biological information may be stored outside the user's wearable device 100, 102 for more than a predetermined period.

As mentioned above, the personal biological data stored on of the wearable device 100, 102 can be used as a way of authenticating the user prior to an operation being performed by a computer system such as a personal computer device 501, 507. More generally, a user of a computer system can be authenticated using a cryptographic "shared secret" derived from the personal biological information. The secret can be derived by applying a cryptographic hash function, e.g. a Secure Hash Algorithm (e.g. SHA-256), to the personal biological data, such that the personal biological data cannot be recovered from the secret.

Generation of the secret can be done by the one or more servers 505 using a stored copy of the personal biological data. The secret is then transmitted to the mobile device 501, 507 and the wearable device 100, 102 using a secure communications channel, e.g. a secure shell (SSH) connection, or by encrypting the secret using a public encryption key obtained from a trusted third-party (e.g. a certificate authority). The copy of the personal biological data may be deleted from the server(s) 505 after the secret has been generated, e.g. so that the only copy of the personal biological data is stored at the wearable device 100, 102 and/or the personal computer device 501, 507.

Alternatively, the secret can be generated by the personal computer device 501, 507 and then sent from the personal computer device 501, 507 to the wearable device 100, 102 over a secure communications channel, e.g. an SSH connection or a wired connection between the two devices. The copy of the personal biological data used to generate the secret may be deleted from the personal computer device 501, 507 after the secret has been generated. As a further alternative, the wearable device 100, 102 may generate the secret and then share it with the personal computer device 501, 507 over a secure communications channel. An advantage of this approach is that it allows the personal biological data to be used for authentication without the personal biological data itself ever needing to be transmitted to the personal computer device 501, 507.

To authenticate the user, a challenge-response protocol can used in which the personal computer device 501, 507 sends the wearable device 100, 102 a challenge request for which the correct response can only be generated using the shared secret. For example, the wearable device 100, 102 may receive cryptographic nonce (e.g. a (pseudo)random number) from the personal computer device 501, 507 and respond with a hash obtained by applying a cryptographic hash function to a combination of the nonce and shared secret. The personal computer device 501, 507 generates a "local" hash in the same way as the wearable device 100, 102. The personal computer device 100, 102 then authenticates the user by verifying that the received hash matches the local hash. It will be appreciated that this method of authenticating users based on personal biological data stored on a wearable device can be carried out using devices other than the wearable device 100, 102 or the personal computer devices 501, 505 described above. In other examples, the wearable device may be a smartphone, smartwatch, or an item of smart clothing, or an implanted device. Similarly, in some examples, the computer system requiring user authentication may be an automatic teller machine, an electronic (e.g. "keyless") lock, a computer system for online banking, an elevator control system or a vehicle ignition system.

The personal biological information used to generate the shared secret may comprise data indicative of the user having a particular DNA sequence or single nucleotide polymorphisms (SNPs), although other data derived from such genetic data can also be used, such as scores indicative of the user's genetic traits. Optionally, the personal biological information may be stored only at the wearable device 100, 102, such that if the wearable device is lost or damaged the user can no longer be authenticated by the computer system (i.e. personal computer device 501, 507 in the example discussed above). When this happens, the shared secret can be re-generated from personal biological data obtained by performing another test (e.g. genetic test) on a biological sample provided by the user. It is preferable that the shared secret is derived from genetic information as, unlike other forms of biometric data (such as retinal or fingerprint data), as generally speaking, a user's genotype does not change over time (e.g. as the user ages).

Although the embodiments and examples described above have focussed on comparing users' genetic traits, the wearable devices 100, 102 can also be used for comparing users' physiological and/or biochemical data and/or data indicative of the users' environment. This data is recorded by one or more sensors of the wearable device 100, 102, such as one or more of the following: pulse rate sensors (e.g photoplethysmography (PPG) sensors; respiration rate sensors; heart rate sensors (also for measuring heart rate variability); blood pressure sensors; microneedles for performing in situ blood tests (e.g. of blood glucose levels); air quality or pollution sensors (e.g. mass spectrometers); and UV light monitors (e.g. photo-diodes). User environmental data may alternatively (or additionally) be obtained by tracking the user's position (e.g. using a global positioning system, GPS, sensor) and using pollution or UV index map data to estimate the user's exposure.

The wearable device 100, 102 stores measurements provided by the sensor(s) along with a timestamp so that users can compare time series data. For example, users may compare how their respective heart rates varied over the course of a physical activity, such as a marathon or cycling race. In some cases, the wearable device 100, 102 integrates the sensor data over time to produce one or more values that can be compared by the users. For example, users who are diabetic can compare how long they were each in a hypoglycaemic state over the past day, week or month, so that they can compare how effectively they each manage their blood-glucose levels. The integrated sensor data may also be used to compare the users' exposure to environmental conditions such as UV light and/or atmospheric pollution (e.g. NOx or particulates).

The physiological, biochemical and/or environmental data can be compared by the wearable devices 100, 102 being brought into contact or close proximity with one another, or using the "remote matching" procedure, as described above. As for genetic traits, the users may select one or more categories of data (such as resting pulse rate, respiration rate, number of steps walked, exposure to pollutants etc) using a user interface provided on the wearable device 100, 102 of the personal computer device 501, 507, e.g. using a smartphone user interface similar to the interface shown in FIG. 4.

Users who are connected to one another within a social network (e.g. a social network populated by user's matching their genetic traits with one another) may also use the social network to compare their data on an ongoing basis. For example, the users' data can be stored by servers associated with the social network to allow users to compare historical data with one another and/or data that is updated dynamically. A users may identify another user of the social network using a search tool, e.g. to lookup the user by name or nickname.

Optionally, the sensors for monitoring physiological and/or biochemical data may be separate from the wearable device 100, 102 so that the sensors can be worn on a different part of the body from the wearable device. Processing of the sensor data may take place either on the wearable device 100, 102 or on the personal computer device 501, 507, after it has been transmitted to the personal computer device using a wired or wireless connection.

The users' physiological, biochemical and/or environmental data may be compared separately from or in combination with the users' data indicative of one or more genetic traits. For example, a user may set (or be set by another user) a target or goal which is determined by the user's genetic traits, such as to achieve a lower resting heart rate (as measured by the wearable device 100, 102) as a result of physical training if the user has a genetic trait associated with hypertension. Two users may each set a goal for one another and each user's progress towards the goal can be compared at intervals, e.g. daily or weekly.

In a preferred embodiment, the physiological, biochemical and/or environmental data is used to modulate product recommendations. The product recommendations are typically derived from the user's genetic traits, as described in U.S. Ser. No. 10/043,590B2 (for example). In one exemplary use case, a product that contains vitamin D may be recommended for a user who is predisposed to needing high levels of vitamin D if the user has not been exposed to enough UV light. Users may compare the number of product recommendations that have been modulated based on physiological, biochemical and/or environmental data. Comparisons can be made for different categories of product, e.g. the number of product recommendations for products containing saturated or unsaturated fats that have been modulated can be compared, which may be of particular interest to users whose genetic traits indicate that they are susceptible to high cholesterol levels.

The modulation of product recommendations provides a "behavioural feedback loop" that helps nudge or encourage/discourage use of certain user behaviour, such as consuming certain products and/or performing certain types of activity. The social experience of comparing data with other users typically has a substantial effect on helping users to change their behaviour. For example, users may support one another as they each try to adjust their behaviour to meet certain goals, such as exercising more to ensure such that the number of modulated product recommendations falls below a threshold number. In this case, the wearable device 100, 102 is typically configured as a state machine that transitions between a "green" (healthy) state in which the number of product recommendations is below a threshold number, and an "amber" state in which more than a threshold number of product recommendations have been modulated as a result of the user's behaviour. The wearable device 100, 102 records the amount of time spent in either state (e.g. over the course of a day) so that users are able to compare how effectively they are each managing their behaviour/lifestyle.

Users may also compete with (or challenge) one another to achieve a pre-agreed goal, e.g. to determine which user has a smaller number of modulated product recommendations over the course of a week (or other period). The targets or goals may be derived from the user's genetic traits to maximise the health benefits for each user and/or to ensure a fair comparison between users with different genetic traits. Rewards or incentives are provided to users in the form of digital trophies or badges associated with an online profile or by offering product discounts to the users (e.g. online discount codes). An indicator on the wearable device 100, 102 can be used to inform the user when another user takes the lead in achieving a particular target. Users may also be sponsored to meet certain goals, e.g. to raise money for a cause or charity that helps with health problems related to a particular genetic trait. Users may also be invited to join one or more online communities or chatrooms depending on their behaviour and/or genetic traits, e.g. so that users can support one another in meeting particular exercise goals or in reducing the amount of particular types of food or drink they consume (with the types of product being determined by the users' genetic traits).

In another preferred embodiment, users are able to match their genetic traits and/or behaviours, as indicated by their physiological, biochemical and/or environmental data, with one or more "virtual profiles" that are associated with users who have given their consent for their genetic traits and/or behavioural data to be compared with other users. In this case, the comparison is "one sided" and users making the comparison are not required to send their data from their wearable device 100, 102 in order to find out whether their data matches that of the virtual profile, i.e. the wearable device 100, 102 of the user associated with the virtual profile is not involved in the comparison. The virtual profile typically comprises genetic traits and behavioural data uploaded from a wearable device 100, 102 worn by a real user, who may be an athlete, sportsperson or a well-known public figure. However, in some cases, the physiological, biochemical and/or environmental data included in the virtual profile may be generated computationally to provide users with a "virtual pacemaker" whose behaviour they can seek to emulate.

It will be appreciated by the person of skill in the art that various modifications may be made to the above described embodiments without departing from the scope of the present invention. For example, as mentioned above, in some cases, only one of two peer users may have a wearable device 100, 102 (i.e. band), with the other only having a smartphone.

The invention claimed is:

1. A computer-implemented method of comparing one or more genetic traits of two users, each user having a wearable device storing data indicative of the one or more genetic traits, the data having been obtained by an analysis of a biological sample provided by the user, the method comprising:
    transmitting the data indicative of the one or more genetic traits from a first of the wearable devices to a first computer device using a short-range wireless data connection;
    transmitting the data from the first computer device to a second computer device over a data network;
    transmitting the data from the second computer device to a second of the wearable devices over a short-range wireless data connection; and
    comparing the data from the first wearable device with the data stored on the second wearable device to determine whether there is a match between the users' one or more genetic traits.

2. A computer-implemented method according to claim 1, further comprising operating an indicator at the second wearable device and/or the second computer device to provide a visual, audio or other sensory indication of whether there is a match between the users' one or more genetic traits.

3. A computer-implemented method according to claim 1, wherein the data indicative of the one or more genetic traits comprises data indicative of nutrition- and/or skin-related genetic traits.

4. A computer-implemented method according to claim 1, wherein each short-range wireless data connection conforms to a Bluetooth protocol, preferably a Bluetooth Low Energy profile, or a near-field communication protocol.

5. A computer-implemented method according to claim 1, wherein each short-range wireless data connection is established by detecting that the respective wearable device is within a predefined distance of, or in contact with, the respective computer device, preferably wherein said predefined distance is less than 10 cm, or more preferably, less than 5 cm.

6. A computer-implemented method according to claim 1, wherein each wearable device is a wrist-worn device and/or each computer device is a portable computer device, preferably a smartphone.

7. A computer-implemented method according to claim 1 and comprising, at the first computer device, receiving an invitation to compare one or more genetic traits with another user.

8. A computer-implemented method according to claim 7, wherein the invitation comprises data indicative of the one or more genetic traits of the other user.

9. A computer-implemented method according to claim 7, wherein the invitation is sent in response to one of the users identifying the other user using an online search tool.

10. A computer-implemented method according to claim 7, wherein the data transmitted from the first wearable device is encrypted using a public encryption key associated with or included in the invitation.

11. A computer-implemented method according to claim 10, wherein the second wearable device stores a corresponding private key for decrypting data encrypted using the public key.

12. A computer-implemented method according to claim 7, further comprising switching the first user device to a mode for establishing a short-range wireless data connection with the first wearable device in response to receiving user input indicative of the invitation being accepted.

13. A computer-implemented method according to claim 12, further comprising forming a connection between the respective users in a social network in response to receiving user input indicative of the invitation being accepted.

14. A computer-implemented method according to claim 7, wherein the user accepts the invitation using the wearable device, preferably by pressing a button on the wearable device or performing a gesture using the wearable device.

15. A computer-implemented method according to claim 1, wherein the data is only made available to the second wearable device if one or more servers of the data network have received data indicative of one or more genetic traits stored on the second wearable device.

16. A computer-implemented method according to claim 1, further comprising, at either of the computer devices or wearable devices, receiving a user selection of which one or more genetic traits are to be compared.

17. A computer-implemented method according to claim 1, wherein the data from the first wearable device is deleted from the second wearable device after a predetermined time.

18. A computer-implemented method according to claim 1, wherein each wearable device stores user activity data indicative of one or more physiological and/or biochemical functions of the user, or indicative of a user environment, the method further comprising, in response to determining that there is a match between the users' one or more genetic traits, comparing the user activity data of the first wearable device with the user activity data of second wearable device to determine whether there is a match between the users' behaviours as indicated by the respective data.

19. A computer-implemented method according to claim 18, wherein each wearable device is configured to provide product recommendations in respect of one or more consumable, topically applied and/or body-worn products, the product recommendations being modulated for each user depending on the user activity data, and wherein the compared user activity data comprises data indicative of one or more product recommendations having been modulated.

* * * * *